US00PP18844P3

(12) United States Plant Patent

Van Der Knaap

(10) Patent No.: US PP18,844 P3

(45) Date of Patent: May 27, 2008

(54) *ANTHURIUM* PLANT NAMED 'BARMODU'

(50) Latin Name: *Anthurium andreanum*
Varietal Denomination: Barmodu

(75) Inventor: Leonardus Johannes Maria Van Der Knaap, Naaldwijk (NL)

(73) Assignee: Knaap Licenties B.V., Naaldwijk (NL)

( * ) Notice: Subject to any disclaimer, the term of this patent is extended or adjusted under 35 U.S.C. 154(b) by 123 days.

(21) Appl. No.: 11/432,643

(22) Filed: May 11, 2006

(65) Prior Publication Data

US 2007/0266467 P1 Nov. 15, 2007

(51) Int. Cl.
*A01H 5/00* (2006.01)

(52) U.S. Cl. ..... Plt./365

(58) Field of Classification Search ..... Plt./265
See application file for complete search history.

*Primary Examiner*—Annette H Para
(74) *Attorney, Agent, or Firm*—Jondle & Associates, P.C.

(57) ABSTRACT

A new *Anthurium* plant particularly distinguished by 5 to 6 flowers with dark-pink, glimmering spathe, lilac-purple spadix, dark glimmering leaves that are narrowly below the flowers, and a compact growth habit, is disclosed.

2 Drawing Sheets

Genus and species: *Anthurium andreanum.*
Variety denomination: 'Barmodu'.

BACKGROUND OF THE NEW PLANT

The present invention comprises a new and distinct cultivar of *Anthurium,* botanically known as *Anthurium andreanum,* and hereinafter referred to by the cultivar name 'Barmodu'. The new cultivar originated from a hybridization made in January 2000 in Massland, The Netherlands. The female parent was the proprietary *Anthurium* plant '20040101-01' (unpatented), while the male parent was the proprietary *Anthurium* plant '20040501-05' (unpatented).

The new cultivar was selected from the results of the hybridization in 2001 and has been asexually reproduced repeatedly by tissue culture in Lochristi, Belgium and Massland, The Netherlands over a five-year period. The present invention has been found to retain its distinctive characteristics through successive asexual propagations.

Plants Breeder's Rights for this cultivar were applied with the European Union on Nov. 15, 2005.

SUMMARY OF THE INVENTION

The following are the most outstanding and distinguishing characteristics of this new cultivar when grown under normal horticultural practices in Massland. The Netherlands.

1) 5 to 6 flowers;
2) Dark-pink glimmering spathe;
3) Lilac-purple spadix;
4) Flowers narrowly above dark, glimmering leaves; and
5) Compact growth habit.

DESCRIPTION OF PHOTOGRAPHS

This new *Anthurium* plant is illustrated by the accompanying photographs which show the overall plant habit including blooms, buds and foliage of the plant; the colors shown are as true as can be reasonably obtained by conventional photographic procedures. The photographs are of a 56-week old plant grown in a greenhouse in Massland, The Netherlands.

DESCRIPTION OF THE NEW CULTIVAR

Figure 1:
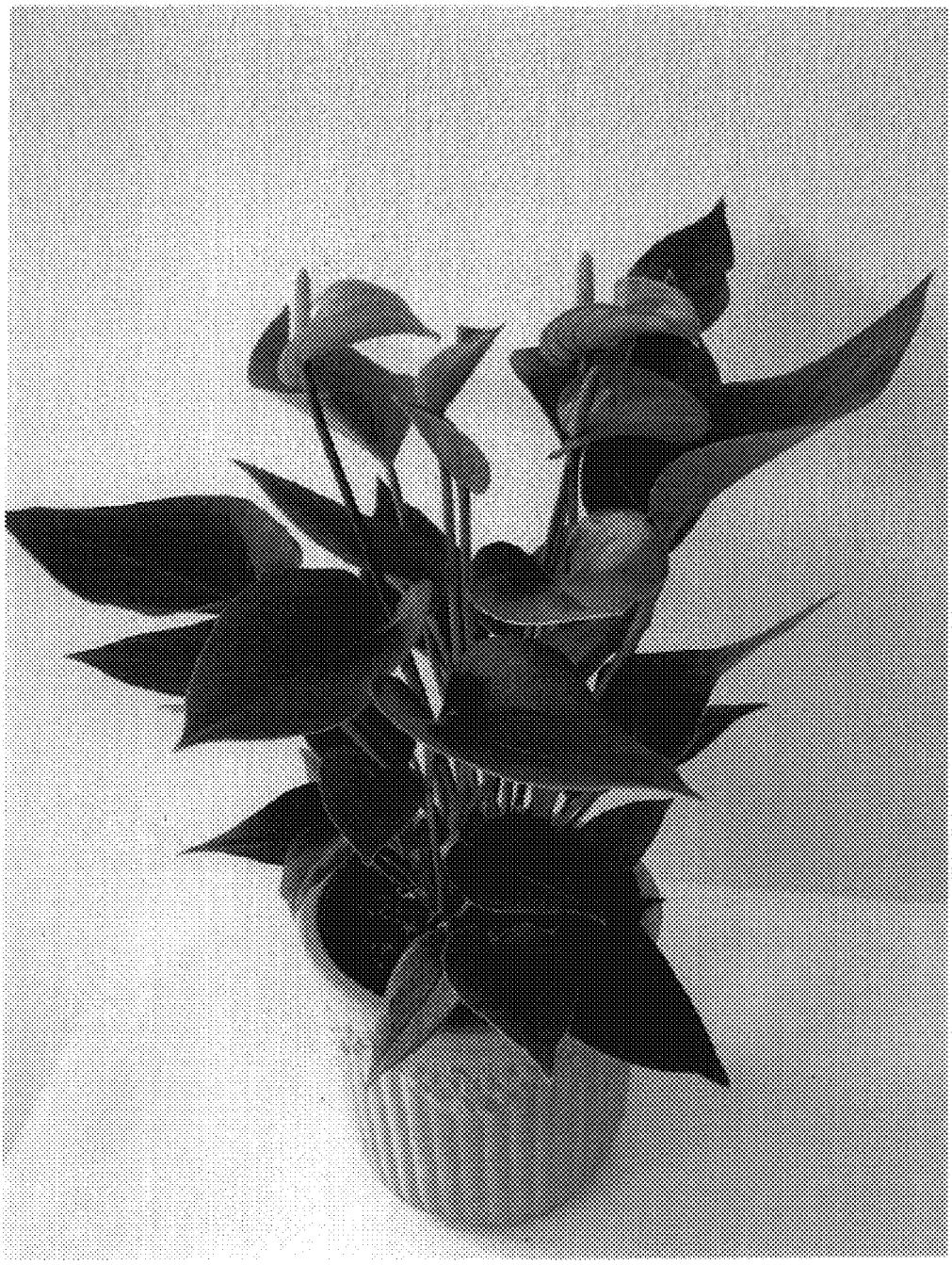
FIG. 1 shows the overall plant habit, including blooms, buds and foliage.
Figure 2:
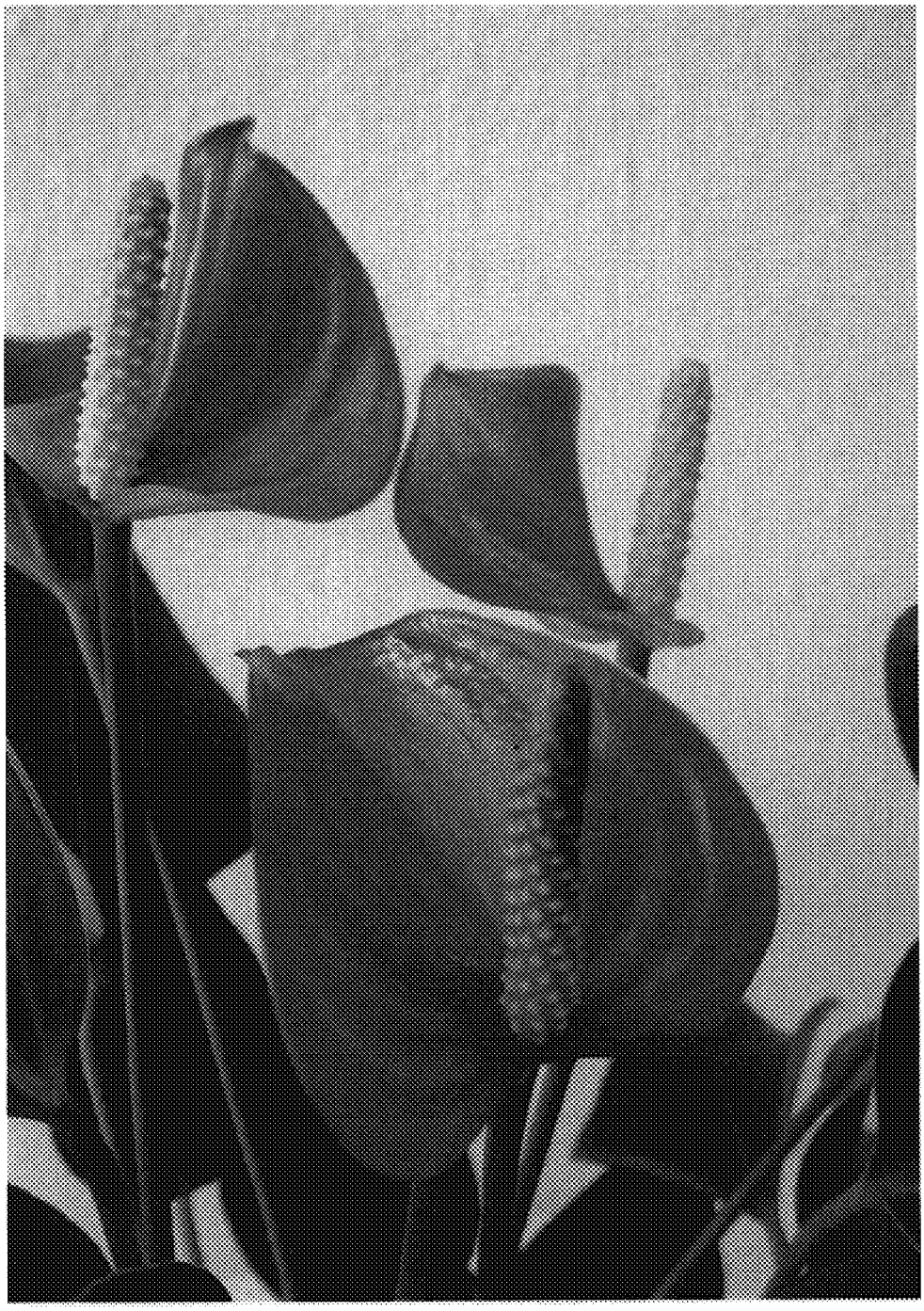
FIG. 2 shows the mature flower.

The following detailed description sets forth the distinctive characteristics of 'Barmodu'. The data which define these characteristics were collected from asexual reproductions carried out in Massland, The Netherlands. The plant history was taken on 56-week old plants which were planted from tissue culture in 14-cm pots and grown in a glass greenhouse between 19° C. and 24° C. Observations were made in the spring of 2006. Color readings were taken under 10 Klux in the greenhouse. Color references are primarily to the R.H.S. Colour Chart of The Royal Horticultural Society of London (R.H.S.) (2001).

DETAILED BOTANICAL DESCRIPTION

Classification:
- *Family.*—Aracea.
- *Botanical.*—*Anthurium andreanum.*
- *Common.*—*Anthurium.*

Parentage:
- *Female parent.*—'20040101-01', a proprietary *Anthurium* plant (unpatented) with pink spathes.
- *Male parent.*—'20040501-05', a proprietary *Anthurium* plant (unpatented) with pink spathes and dark-purple spadix.

Propagation:
- *Propagation.*—Tissue culture.
- *Time to initiate and develop roots.*—10 days (under in vitro conditions).
- *Root description.*—RHS 159A to RHS 37B, freely branching, fine, fleshy with average density.

*Time to produce a finished flowering plant.*—56 weeks for a 14 cm pot.

Plant:

*Form/shape.*—Herbaceous perennial.

*Growth habit.*—Upright.

*Height (measured from soil, including inflorescence).*—25 cm to 30 cm.

*Width (measured from leaf tips).*—40 cm to 45 cm.

*Keeping quality.*—90 days.

Leaves:

*Arrangement.*—From the ground.

*Immature leaves.*—Length: 6 cm to 8 cm. Width: 4 cm to 5 cm. Color: Upper surface: Darker than RHS 144A. Lower surface: RHS 144A. Texture: Smooth to leathery.

*Mature leaves.*—Length (fully expanded): 15 cm to 17 cm. Width: 10 cm. Shape: Cordate. Margin: Entire. Apex: Apiculate to cuspidate. Base: Subcordate. Color: Upper surface: Closest to RHS 147A. Lower surface: Closest to RHS 144A. Texture: Leathery. Venation: Pinnate. Venation color: Upper surface: Closest to RHS 144A. Lower surface: Closest to RHS 144B.

*Petiole.*—Length: 5 cm to 20 cm. Diameter: 0.2 cm to 0.3 cm. Color: RHS 144A, oldest petioles overlain with anthocyan coloration. Texture: Smooth, leathery.

*Geniculum.*—Length: 1.5 cm to 2.0 cm. Width: 0.2 cm to 0.3 cm. Color: Upper surface: RHS N199A to RHS N199B. Lower surface: Closest to RHS 144A. Texture: Less smooth than petiole.

*Wing.*—Length: Almost absent to 3 cm. Width: 0.1 cm to 1.0 cm. Color: RHS 144C to RHS 144D.

Inflorescence:

*Arrangement.*—Single.

*Flowering habit (length of flowering season).*—Continuous.

*Number of inflorescences per plant.*—About 5 to 6.

*Fragrance.*—Absent.

*Lastingness of individual blooms.*—90 days.

Spathe:

*Shape.*—Cordate.

*Apex.*—Apiculate to cuspidate.

*Base.*—Cordate.

*Margin.*—Entire.

*Texture.*—Leathery, somewhat blistered.

*Size.*—Length: 6 cm to 7 cm. Width: 4.5 cm to 6.0 cm.

*Color.*—Immature: Front surface: Closest to RHS 54A. Rear surface: Closest to RHS N66D. Towards the base: RHS 54B to RHS 54C. Mature: Front surface: Closest to RHS 52B. Rear surface: Closest to RHS 63D. Towards the base: RHS 54C, with RHS 147A dark veins.

Spadix:

*Size.*—Length: 3.5 cm to 4.0 cm. Diameter (at apex): About 0.6 cm. Diameter (at base): About 0.7 cm.

*Shape.*—Straight, erect.

*Apex.*—Rounded.

*Base.*—Fused with spathe.

*Texture.*—Shiny.

*Color.*—Immature: RHS 39B at base to RHS 145B at apex. Mature: Closest to RHS 159A.

Flowers:

*Quantity per spadix.*—150 to 200.

*Shape.*—Rounded.

*Size.*—Length: 0.05 cm to 0.1 cm. Diameter (max): 0.1 cm.

Color: RHS 159B.

Reproductive organs:

*Stamens.*—Not observed.

*Pistils.*—Quantity: 150 to 200. Length: Not observed.

*Style.*—Not observed.

*Stigma.*—Shape: Ovoid. Diameter: About 0.05 cm. Color: RHS 155B.

*Ovary.*—Shape: Square. Color: RHS 54D.

Fruit and seed set: Immature seed color: RHS 114B.

Disease and insect resistance: No particular resistance or susceptibility different from other *Anthurium* varieties.

COMPARISON WITH PARENTAL AND COMMERCIAL CULTIVARS

'Barmodu' differs from the female parent '20040101-01' (unpatented), by having dark-pink, lancet-shaped spathe, while '20040101-01' has pink, more rounded-shaped spathe. In addition, 'Barmodu' has a compact plant habit and lancet-shaped leaves, while '20040101-01' has a more stretched plant habit and *Anthurium andreanum*-shaped leaves.

'Barmodu' differs from the male parent '20040501-05' (unpatented), by having dark-pink, large, lancet-shaped spathe and lilac-purple spadix, while '20040501-05' has pink, medium, round-shaped spathe and dark-purple spadix. In addition, 'Barmodu' has medium to large leaves, while '20040501-05' has small to medium leaves.

'Barmodu' differs from the commercial variety 'Bossalo' (unpatented), by having dark-pink spathe and lilac-purple spadix, while 'Bossalo' has red spathe and white-yellow spadix. In addition, 'Barmodu' has glimmering flowers and lancet-shaped glimmering leaves, while 'Bossalo' has dull flowers and *Anthurium andreanum*-shaped, dull leaves.

I claim:

1. A new and distinct cultivar of *anthurium* plant as shown and described herein.

* * * * *